United States Patent
Suckau et al.

(10) Patent No.: US 10,877,044 B2
(45) Date of Patent: Dec. 29, 2020

(54) TARGETED PROTEIN CHARACTERIZATION BY MASS SPECTROMETRY

(71) Applicant: Bruker Daltonik GmbH, Bremen (DE)

(72) Inventors: Detlev Suckau, Grasberg (DE); Anja Resemann, Ganderkesee (DE); Waltraud Evers, Delmenhorst (DE)

(*) Notice: Subject to any disclaimer, the term of this patent is extended or adjusted under 35 U.S.C. 154(b) by 21 days.

(21) Appl. No.: 16/429,591

(22) Filed: Jun. 3, 2019

(65) Prior Publication Data
US 2019/0376980 A1 Dec. 12, 2019

Related U.S. Application Data

(60) Provisional application No. 62/681,411, filed on Jun. 6, 2018.

(51) Int. Cl.
| | |
|---|---|
| G01N 33/68 | (2006.01) |
| H01J 49/00 | (2006.01) |
| H01J 49/16 | (2006.01) |
| H01J 49/40 | (2006.01) |
| G01N 33/94 | (2006.01) |

(52) U.S. Cl.
CPC .......... *G01N 33/6851* (2013.01); *G01N 33/94* (2013.01); *H01J 49/0027* (2013.01); *H01J 49/164* (2013.01); *H01J 49/40* (2013.01); *G01N 2440/38* (2013.01); *G01N 2560/00* (2013.01)

(58) Field of Classification Search
CPC ............... G01N 33/6851; G01N 33/94; G01N 2560/00; H01J 49/00; H01J 49/0027; H01J 49/164; H01J 49/40
USPC ................ 250/281, 282, 283, 288
See application file for complete search history.

(56) References Cited

U.S. PATENT DOCUMENTS

| | | | |
|---|---|---|---|
| 2002/0102610 A1* | 8/2002 | Townsend | G16B 30/00 435/7.1 |
| 2005/0153380 A1 | 7/2005 | Everett et al. | |
| 2005/0288865 A1 | 12/2005 | Appel et al. | |
| 2007/0092926 A1 | 4/2007 | Alterman et al. | |
| 2015/0066380 A1* | 3/2015 | Yao | H01J 49/0036 702/19 |
| 2019/0072546 A1* | 3/2019 | Bergo | G01N 33/6848 |

OTHER PUBLICATIONS

Henzel, W. J. et al., "Identifying proteins from two-dimensional gels by molecular mass searching of peptide fragments in protein sequence databases", Proc. Natl. Acad. Sci. USA, vol. 90, Jun. 1993, pp. 5011-5015.

(Continued)

*Primary Examiner* — Nicole M Ippolito
(74) *Attorney, Agent, or Firm* — Benoit & Côté Inc.

(57) ABSTRACT

The invention provides methods for characterizing a target protein wherein a mass spectrum of digest peptides of the target protein is acquired and compared with measured reference mass spectra of digest peptides of reference proteins or of proteins of reference host cells. The comparison comprises determining similarity scores of the intensity patterns of the mass spectrum and the reference mass spectra. The characterization comprises assigning the target protein to a reference protein having a reference mass spectrum with a similarity score above a predetermined threshold.

20 Claims, 2 Drawing Sheets

(56) References Cited

OTHER PUBLICATIONS

Quadroni J.P. et al., "Protein Identification by Mass Profile Fingerprinting", Biochemical Biophysical Research Communications, Aug. 1993, pp. 58-64.
Mann, M. et al., "Use of Mass Spectrometric Molecular Weight Information to Identify Proteins in Sequence Databases", Biological Mass Spectrometry, vol. 22, 1993, pp. 338-345.
Pappin, D.J.C. et al., "Rapid identification of proteins by peptide-mass fingerprinting" Current Biology. vol. 3, 1993, pp. 327-332.
Yates, John R., "Peptide Mass Maps: A Highly Informative Approach to Protein Identification" Analytical Biochemistry vol. 214, 1993, pp. 397-408.
Cottrell, John, "Database Searching for Protein Identification and Characterization", Matrix Science, 2004.
Parker, K.C., "Scoring Methods in MALDI Peptide Mass Fingerprinting: ChemScore, and the ChemApplex Program" American Society for Mass Spectrometry, Nov. 19, 2001.
Narasimhan C. et al., "MASPIC: Intensity-Based Tandem Mass Spectrometry Scoring Scheme That Improves Peptide Identification at High Confidence", Analytical Chemistry, vol. 77, 2005, p. 7581-7593.
Karger A. et al., "Rapid identification of Burkholderia mallei and Burkholderia pseudomallei by intact cell Matrix-assisted Laser Desorption/Ionisation mass spectrometric typing", BMC Microbiology, vol. 12, 2012, p. 229.
Cottrell J.S., "Protein identification using MS/MS data", Journal of Proteomics, vol. 74, 2011, p. 1842-1851.

\* cited by examiner

TARGETED PROTEIN CHARACTERIZATION BY MASS SPECTROMETRY

BACKGROUND OF THE INVENTION

The routine identification of proteins by peptide mass fingerprinting (PMF) of their digest products has been known for 25 years. In 1993, five scientific working groups each published the basics of this method: (1) Henzel, W. J., Billeci, T. M., Stults, J. T., Wong, S. C., Grimley, C. and Watanabe, C. (1993). Proc Natl Acad Sci USA 90, 5011-5; (2) James, P., Quadroni, M., Carafoli, E. and Gonnet, G. (1993). Biochem Biophys Res Commun 195, 58-64; (3) Mann, M., Hojrup, P. and Roepstorff, P. (1993). Biol Mass Spectrom 22, 338-45; (4) Pappin, D. J. C., Hojrup, P. and Bleasby, A. J. (1993). Curr. Biol. 3, 327-32; and (5) Yates, J. R., 3rd, Speicher, S., Griffin, P. R. and Hunkapiller, T. (1993). Anal Biochem 214, 397-408.

The method became an enormous success and was widely used. A detailed historic review with the title "Protein Identification: The Origins of Peptide Mass Fingerprinting" is given by W. J., Henzel, C. Watanabe, and J. T. Stults, J Am Soc Mass Spectrom. 2003, 14, 931-942.

In an ASMS Tutorial from 2004, John Cottrell taught: "Peptide mass fingerprinting can only be used with a pure protein or a very simple mixture. The protein is digested with an enzyme of high specificity; usually trypsin, but any specific enzyme may be used. The resulting mixture of peptides is analyzed by mass spectrometry. This yields a set of molecular mass values, which are searched against a database of protein sequences using a search engine. For each entry in the protein database, the search engine simulates the known cleavage specificity of the enzyme, calculates the masses of the predicted peptides, and compares the set of calculated mass values with the set of experimental mass values. Some type of scoring is used to identify the entry in the database that gives the best match, and a report is generated."

Peptide mass fingerprinting thus utilizes only the masses of the peptides. Usually, intensities do not play a role because they scarcely can be calculated by the computer's virtual cleavage program. John Cottrell: "In a peptide mass fingerprint, it is the mass values of the peaks that matter most. The peak area or intensity values are a function of peptide basicity, length, and several other physical and chemical parameters. There is no particular reason to assume that a big peak is interesting and a small peak is less interesting. . . . Mass accuracy is important, but so is coverage. Better to have a large number of mass values with moderate accuracy than one or two mass values with very high accuracy."

There are more than half a dozen peptide mass fingerprinting programs available on the Web, and many more are described in the literature.

In contrast to using only the mass values, an attempt to consider calculated peak intensities was made by K. C. Parker: "Scoring methods in MALDI Peptide Mass Fingerprinting: ChemScore, and the ChemApplex Program". (J Am Soc Mass Spectrom 2002, 13, 22-39). The author describes a software program (ChemApplex) based on a calculated parameter (Combined Protein Score) that takes into account (1) peak intensity, (2) the mass accuracy of the match, and (3) ChemScore, a theoretical intensity factor that estimates the probability of observing a particular peptide based on a combination of chemical considerations, in particular the amino acid composition of the peptide and the amino acid sequence of the amino acids that span the cleavage site.

The publication US 2007/0092926 A1 (M. A. Alterman and B. A. Kornilayev; 2007) describes the use of a "unique proteolytic peptide" for peptide mass fingerprinting. The term "distinctive proteolytic peptide" or "unique proteolytic peptide" embraces a compound comprised of subunit amino acids linked by peptide bonds generated by proteolytically cleaving a protein with a protease, which differs from any other proteolytic peptide derived from digestion of other proteins using the same protease. Preferably, the distinctiveness or uniqueness refers to the entire genome, and most preferably to the human genome, when referenced against the SwissProt or NCBI databases. The peptide's boundaries may be determined by predicting the cleavage sites of a protease.

A qualitative and quantitative analysis of targeted proteins as described in publication US 2005/0153380 A1 (N. P. Everett et al., 2005) is based on "signature peptides" for the same purpose. The targeted proteins are extracted and concentrated from mixtures. Examples of appropriate means for concentration include the use of solid support resins (e.g., ion exchangers, affinity gel, and other resins that adsorb proteins). The term "signature peptide masses" refers to the peptide masses generated from a particular protein target or targets, which can be used to identify the protein target. Those peptide masses from a given peptide mass fingerprint which ionize easily and have a high mass resolution and accuracy, are considered to be members of a set of signature diagnostic peptide masses for a given target. The pattern is unique and thus distinct for each protein.

Considering biopharmaceutical development (e.g., clone selection) and production (e.g., rapid identity testing for Fill & Finish operation) there is a requirement for fast but highly reliable analysis with short return times to accelerate decision-making and reduce costs. In the production of biopharmaceuticals there might arise the added complexity of several product molecules being highly similar. For example, different therapeutic antibodies of the same class (e.g., IgG1κ) cannot be reliably distinguished based on the Sequence Coverage obtained from a common peptide mass fingerprint and currently require LC-MS or dedicated ELISAs to achieve specific identification. A fast and reliable method is described that can be applied specifically to a set of highly related molecules (monoclonal antibodies such as Herceptin or Adalimumab).

SUMMARY OF THE INVENTION

In a first aspect, the invention provides a method for characterizing a target protein, comprising the steps of: providing a library of measured reference mass spectra of reference proteins wherein each reference mass spectrum is acquired for an enzymatic digest of one reference protein and the conditions of the enzymatic digest are substantially equal for all reference proteins; enzymatically digesting the target protein under the same conditions used for the reference proteins; acquiring a mass spectrum for the enzymatically digested target protein; determining similarity scores of the intensity pattern of the mass spectrum and the reference mass spectra; and characterizing the target protein by assigning the target protein to a reference protein having a reference mass spectrum with a similarity score above a predetermined threshold. The target protein is generally a protein from a sample to be characterized.

The method compares the similarities of mass positions and intensities of the measured mass spectrum with those of measured reference mass spectra of reference proteins in a library. A particular advantage of this approach is that it accounts for the fact that the spectra of two highly similar reference proteins, even though digested using identical digest peptides, may vary in their intensity patterns due to different relative intensities of their digest peptides. The similarity scores are preferably determined by the cosine similarity measure or a cross-correlation.

The enzymatic digest preferably uses at least one of trypsin, Ides and Lys-C. The target protein and the reference proteins are equally denatured by a reducing agent and by a denaturing agent prior to the enzymatic digest. The denaturing and the enzymatic digest can be performed in less than 30 minutes, in particular in less than 15 minutes. Preferably, dithiothreitol (DTT) with rifluorethanol (TFE) is used as denaturing solution.

The mass spectrum of the digested target protein and the reference mass spectra are preferably acquired by a MALDI-TOF mass spectrometer. More preferably, the MALDI-TOF mass spectrometer comprises a reflector. The MALDI-TOF mass spectrometer can be a bench top instrument having a footprint of less than one square meter and a height of less than 1.5 meters.

In a preferred embodiment, the reference proteins have different amino acid sequences and the enzymatic digest of the reference proteins comprises digest peptides with masses specific to the corresponding reference protein. The target protein is identified by the assignment to one of the reference proteins. The target protein can, for example, be extracted from a complex sample mixture by affinity capture. The complex mixture can be one of urine, plasma, serum, spinal fluid and lysed tissue cells. Preferably, an antibody is used for the affinity capture.

In another embodiment, the target protein is a biopharmaceutical, in particular from production. In this case, the reference proteins are different protein isoforms of the target biopharmaceutical which are formed by at least one of alternative splicings, sequence variations, post-transcriptional modifications, and stress-induced modifications. The target protein is identified as one of the isoforms by assignment to one of the reference proteins. The post-transcriptional modification can at least be one of glycosylation, oxidation, acetylation and amidation.

In another embodiment, the target protein is an antibody, in particular from production. In this case, the reference proteins are different modifications of the antibody. The target protein and the reference proteins are enzymatically digested into domains and the target protein is identified to be modified by assignment to one of the reference proteins. The modifications can at least be one of glycosylation, oxidation, acetylation and amidation. Preferably, the enzyme IdeS is used to prepare Fc/2 antibody domains for glycoprofiling. One reference protein can be the desired antibody and the target protein is identified to be the desired antibody by assignment to this reference protein.

Preferably, the method further comprises that redundant mass signals which are present in a majority of the measured reference mass spectra are removed and reduced reference mass spectra are provided and/or used in the determining step. The reduced set preferably comprises approximately three to fifteen mass signals. If the reference proteins have different amino acid sequences, the reduced mass reference spectra preferably comprise only the mass signals of digest peptides which are characteristic for the corresponding reference protein. The reduced reference mass spectra can additionally comprise some abundant mass signals which are present in substantially all or many reduced reference mass spectra and the number of the abundant mass signals is lower than the number of the characteristic mass signals. To determine the redundant mass signals in the measured reference mass spectra of a library, a multivariate statistical method is used. The multivariate statistical method is preferably one of Principal Component Analysis (PCA), Hierarchical Clustering (HC), Receiver Operator Curves (ROC) and Probabilistic Latent Semantic Analysis (pLSA).

In a second aspect, the invention provides a method for characterizing proteins of target host cells, comprising the steps of: providing a library of measured reference mass spectra of proteins of reference host cells wherein each reference mass spectrum comprises mass signals of digest peptides which are generated by an enzymatic digest of the proteins of one type of reference host cells and are extracted after the enzymatic digest by affinity capture using multiple affinity agents; enzymatically digesting the proteins of the target host cells under the same conditions used for the proteins of the reference host cells and then extracting the digest peptides by affinity capture using the multiple affinity agents; acquiring a mass spectrum for the extracted digest peptides of the target host cells; determining similarity scores of the intensity pattern of the mass spectrum and the reference mass spectra; and characterizing the target host cell by assigning the proteins of the target host cells to a type of reference host cells having a reference spectrum with a similarity score above a predetermined threshold.

The method compares the similarities of mass positions and intensities of the measured mass spectrum with those of measured reference mass spectra in a library. A particular advantage of this approach is that it accounts for the fact that the spectra of two highly similar reference mass spectra may comprise mass signals at the same mass positions, but vary in the intensity pattern, primarily due to the different relative intensities of the digest peptides. The similarity scores are preferably determined by the cosine similarity measure or a cross-correlation.

DETAILED DESCRIPTION

Figure 1:
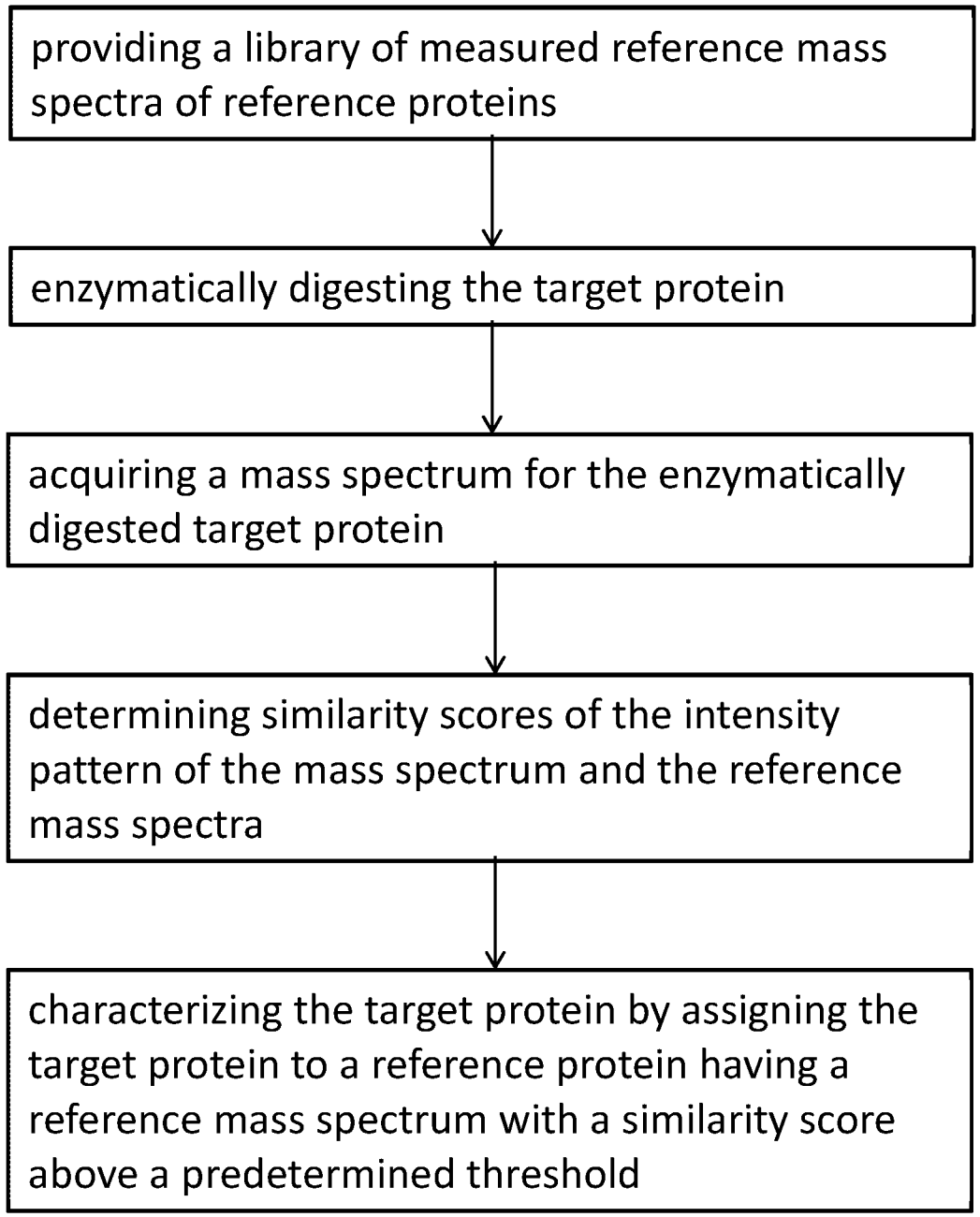
FIG. 1 illustrates a schematic workflow of a method for characterizing a target protein according to the present invention.
Figure 2:
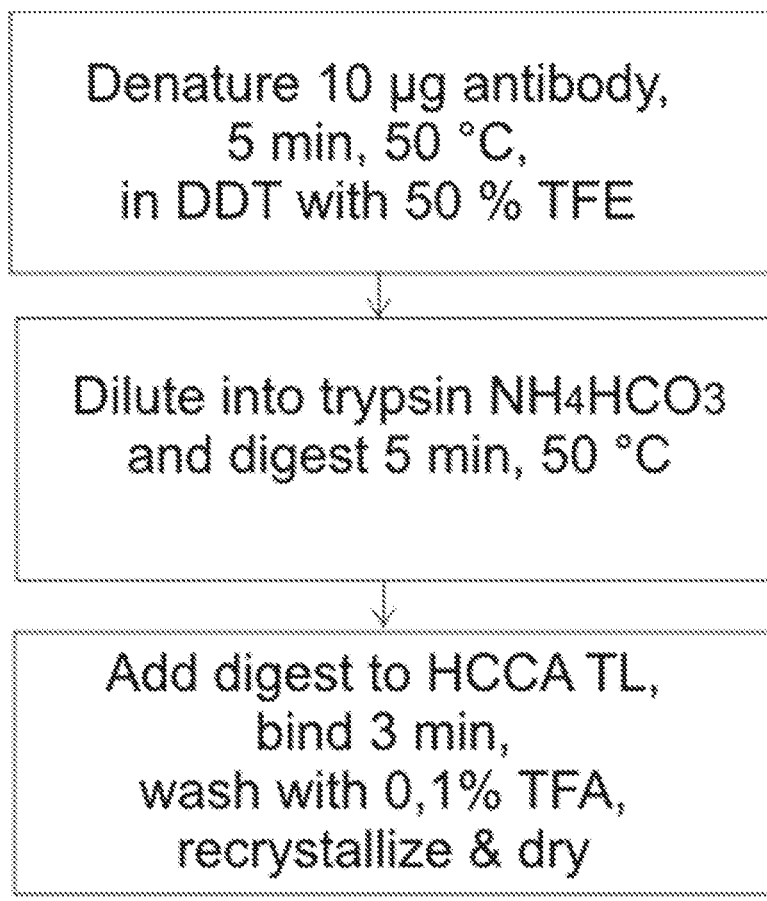
FIG. 2 illustrates the preferred workflow for a fast denaturing and digestion of a target protein.

The invention provides a preferred method for identifying a target protein by peptide mass fingerprinting (PMF) of the peptide mixture produced by enzymatic digestion of the target protein by a protease such as trypsin, particularly a method for affirming the identity for quality assurance. The identification will be based, quite differently from the usual peptide mass fingerprinting, on the similarity of the measured intensity pattern of the target protein with the measured intensity pattern of the reference proteins.

Whereas known peptide mass fingerprinting relies on peptide masses virtually calculated from amino acid sequences found in libraries, the new method compares the similarities of masses and intensities of a measured mass spectrum with those of measured reference mass spectra of reference proteins in a library. A particular advantage of this approach is that it accounts for the fact that even identical digest peptides of two highly similar reference proteins may be represented in the two corresponding reference mass spectra, but produce mass signals that vary drastically in their relative intensities due to different physicochemical microenvironments near the cleavage sites.

Any suitable program may be used which determines the intensity pattern similarity between the mass spectrum of the target protein and the reference mass spectra of the reference proteins that form the library. As an example, the similarity of the intensity pattern can be rapidly determined by forming the cosine of the angle between the vectors formed by the intensity pattern (cosine similarity score) or by cross-correlation.

The reference spectra of reference proteins are preferably reduced to a smaller set of specific mass signals with their intensities (subset profile) which results in an improved specificity of the assignment. The reduced set preferably comprises approximately three to fifteen peptides. There are different ways available to generate such subset profiles. Such methods include typical statistical methods for spectra classification such as Principal Component analysis (PCA), Hierarchical Clustering (HC) or Receiver Operator Curves (ROC) to name some of these methods. If the reference proteins are antibodies, characteristic digest peptides can be determined from the complementarity determining regions (CDRs). The selection of the specific mass signals has to be repeated if the library is enlarged by the addition of further reference mass spectra. Optionally, a few abundant redundant peptide mass signals can be added for quality control.

The method is preferably performed with rapid protein denaturing and digesting methods, typically in less than 30 minutes and, in particular, in less than 15 minutes. The resulting peptide mixture will be prepared with matrix solution to produce a sample spot on a mass spectrometric sample support plate for use in time-of-flight mass spectrometers with ionization by matrix-assisted laser desorption (MALDI). Reasonably priced table-top time-of-flight reflector mass spectrometers may be used for spectrum acquisition.

The method of the invention can be used particularly in antibody production quality control, or in clone selection workflows during pharmaceutical development, e.g., to screen glycan profiles in intact Fc-domains or for clones properly carrying the target sequence, based on differentiating relative intensity patterns in the reference mass spectra of the digest peptides of the reference proteins. For the characterization of an antibody, protocols can be used to achieve a result from providing the antibody to the automatic identification within 15 minutes, in particular protocols based on trypsin/Lys-C digests.

The target proteins and the reference proteins may be rapidly denatured using a mixture of reducing and denaturing agents such as dithiothreitol and trifluorethanol, and rapidly digested by a protease such as trypsin or serial or parallel double-digest (e.g.,Trypsin/Lys-C). The peptide mixture may be prepared with a matrix substance for ionization by matrix assisted laser desorption (MALDI). HCCA (α-cyano-4-hydroxycinnamic acid) may be used as matrix substance.

The methods, however, can also be applied to targeted proteins which are present in a complex substance mixture. The targeted protein then has to be extracted and purified. To avoid time-consuming methods such as HPLC, for instance, fast purification methods have to be applied. Examples are solid phase extraction, affinity capture on column or on magnetic beads, and the like.

Example for a rapid protein identity testing embodiment: The digest time including denaturation, reduction and proteolytic digestion is reduced to 15 min. with subsequent MALDI sample preparation including a simple on-target purification step. The quality of the MALDI peptide mass fingerprints achieved from all tested antibody digests is high (70% sequence coverage) and enables an identity assay that is substantially based on the differentiation peptides only, i.e., peptides derived from the variable N-termini of ~120 residues of the antibodies; 4-13 peptides are used in these profiles in addition to six abundant common peptides. Profiles of these antibodies allow for their distinction based on cosine similarity scoring (CSS) with CCS>0.9 as acceptance criterion, non-matching identities yield CCS values of 0.2-0.6. In addition, butterfly plots allow the visual confirmation of the ID provided by the software.

Example for an embodiment procedure for clone selection: Digest and sample preparation time of IdeS digestion and MALDI sample preparation is about 30 minutes. Major glycans such as G0F, G1F, G2F and G3F are assayed by direct profiling of the Fc-domain of monoclonal antibodies—together with the proper state of the Fc C-terminus. Spectra acquisition and processing are completed in less than 10 sec/sample. Different attributes such as the match of the glycan profile with a reference profile with a certain score or the test for G0F as being the base peak glycan are reported in the software. Automation and parallelization of sample processing in the clone selection workflow permit hundreds of samples to be assessed per day with a high degree of automation and drastically accelerate clone-selection based on major Fc-glycans.

The invention further provides a preferred method for characterizing proteins of target host cells. Here, anti-peptide antibodies are used to extract digest peptides of the proteins of the target host cells after a tryptic digestion. Typically, stable isotope labelled standard peptides (SIS-peptides) can be additionally added after digestion, so that the SIS-peptides and the native peptide obtained by trypsin digestion can be jointly extracted with an anti-peptide antibody. Multiple antibodies (either a polyclonal antibody or a pool of monoclonal antibodies) and SIS-peptides can now be used together in the analysis to extract 5, 10 or more peptides specific to a host cell protein (HCP) analysis. The profile would now be defined with the SIS-peptide mass signals and the intensity at a level relevant for each host cell protein. The native peptide intensity can then be determined based on the peak intensity ratio native/SIS peptides and deviations from the target HPC levels automatically detected and accurately be quantified.

The invention claimed is:

1. A method for characterizing a target protein, comprising the steps of:
   providing a library of measured reference mass spectra of reference proteins wherein each reference mass spectrum is acquired for an enzymatic digest of one reference protein and the conditions of the enzymatic digest are substantially equal for all reference proteins;
   enzymatically digesting the target protein under the same conditions used for the reference proteins;
   acquiring a mass spectrum for the enzymatically digested target protein;
   determining similarity scores for intensity patterns of the mass spectrum and the reference mass spectra; and
   characterizing the target protein by assigning the target protein to a reference protein having a reference mass spectrum with a similarity score above a predetermined threshold.

2. The method according to claim 1, wherein the enzymatic digest uses at least one of trypsin, Ides and Lys-C.

3. The method according to claim 2, wherein the target protein and the reference proteins are equally denatured by a reducing agent and by a denaturing agent prior to the enzymatic digest.

4. The method according to claim 1, wherein the mass spectrum of the digested target protein and the reference mass spectra are acquired by a MALDI-TOF mass spectrometer.

5. The method according to claim 1, wherein the reference proteins have different amino acid sequences, the enzymatic digests of the reference proteins comprise digest peptides each having masses specific to the corresponding reference protein and the target protein is identified by assignment to one of the reference proteins.

6. The method according to claim 1, wherein the target protein is extracted from a complex sample mixture by affinity capture.

7. The method according to claim 6, wherein the complex mixture is one of urine, plasma, serum, spinal fluid and lysed tissue cells.

8. The method according to claim 6, wherein an antibody is used for the affinity capture.

9. The method according to claim 1, wherein the target protein is a biopharmaceutical.

10. The method according to claim 9, wherein the reference proteins are different protein isoforms of the biopharmaceutical which are formed by at least one of alternative splicings, sequence variations, post-transcriptional modifications and stress-induced modifications, and the target protein is identified as one of the isoforms by assignment to one of the reference proteins.

11. The method according to claim 1, wherein the target protein is an antibody.

12. The method according to claim 11 wherein the reference proteins are different modifications of the antibody, the target protein and the reference proteins are enzymatically digested into domains and the target protein is identified to be modified by assignment to one of the reference proteins.

13. The method according to claim 12, wherein the modifications are at least one of glycosylation, oxidation, acetylation and amidation.

14. The method according to claim 13, wherein the enzyme IdeS is used to prepare Fc/2 antibody domains for glycoprofiling.

15. The method according to claim 12, wherein one reference protein is the antibody and the target protein is identified to be the antibody by assignment to this reference protein.

16. The method according to claim 1, wherein redundant mass signals which are present in a majority of the measured reference mass spectra are removed, and reduced reference mass spectra are provided and/or used for the determining step.

17. The method according to claim 16, wherein the reference proteins have different amino acid sequences, the enzymatic digest of the reference proteins comprises digest peptides with masses which are characteristic for the corresponding reference protein and reduced reference mass spectra comprise only the characteristic mass signals.

18. The method according to claim 16, wherein the reduced reference mass spectra additionally comprise some abundant mass signals which are present in substantially all reduced reference mass spectra and the number of the abundant mass signals is lower than the number of the characteristic mass signals.

19. The method according to claim 1, wherein the similarity scores are determined by a cosine similarity measure or a cross-correlation.

20. A method for characterizing proteins of target host cells, comprising the steps of:
providing a library of measured reference mass spectra of proteins of reference host cells wherein each reference mass spectrum comprises mass signals of digest peptides which are generated by an enzymatic digest of multiple proteins of one type of reference host cells and are extracted by affinity capture using multiple affinity agents after the enzymatic digest;
enzymatically digesting the proteins of the target host cells under the same conditions used for the proteins of the reference host cells and then extracting the digest peptides by affinity capture using the multiple affinity agents;
acquiring a mass spectrum for the extracted digest peptides of the target host cells;
determining similarity scores of the intensity pattern of the mass spectrum and the reference mass spectra; and
characterizing the target host cells by assigning the proteins of the target host cells to a type of reference host cell having a reference spectrum with a similarity score above a predetermined threshold.

* * * * *